United States Patent [19]

Goodnight, Jr.

[11] Patent Number: 4,478,715
[45] Date of Patent: Oct. 23, 1984

[54] COLUMN RETAINER

[75] Inventor: Lyman E. Goodnight, Jr., North Palm Beach, Fla.

[73] Assignee: Milton Roy Company, St. Petersburg, Fla.

[21] Appl. No.: 547,977

[22] Filed: Nov. 2, 1983

[51] Int. Cl.³ ............................................. B01D 15/08
[52] U.S. Cl. .................................... 210/198.2; 55/386
[58] Field of Search ........................ 210/198.2; 55/386

[56] References Cited

U.S. PATENT DOCUMENTS 4,083,702 4/1978 Hartigan et al. ...................... 55/386
4,084,718 4/1978 Wadsworth ...................... 210/198.2
4,093,550 6/1978 Stahl ................................. 210/198.2
4,390,032 8/1983 Mott ................................. 210/198.2

FOREIGN PATENT DOCUMENTS 52-8892 1/1977 Japan ............................... 210/198.2

Primary Examiner—John Adee
Attorney, Agent, or Firm—Carroll F. Palmer

[57] ABSTRACT

The liquid chromatographic column (LCC) in liquid chromatography apparatus (LCA) is connected to another fluid flow member, e.g., an injection valve and/or a detector, via a column retainer that comprises a collet with split, tapered distal end that threads into a collet nut having an internal tapered lumen to cause the collet split end to compress about the outside of the liquid chromatographic column so that the retainer assembly may hold the column without damage to it in connected position with the other fluid flow member. The column retainer may include a retainer nut that serves to hold the retainer assembly onto the fluid flow member by threading into a female opening in it.

4 Claims, 5 Drawing Figures

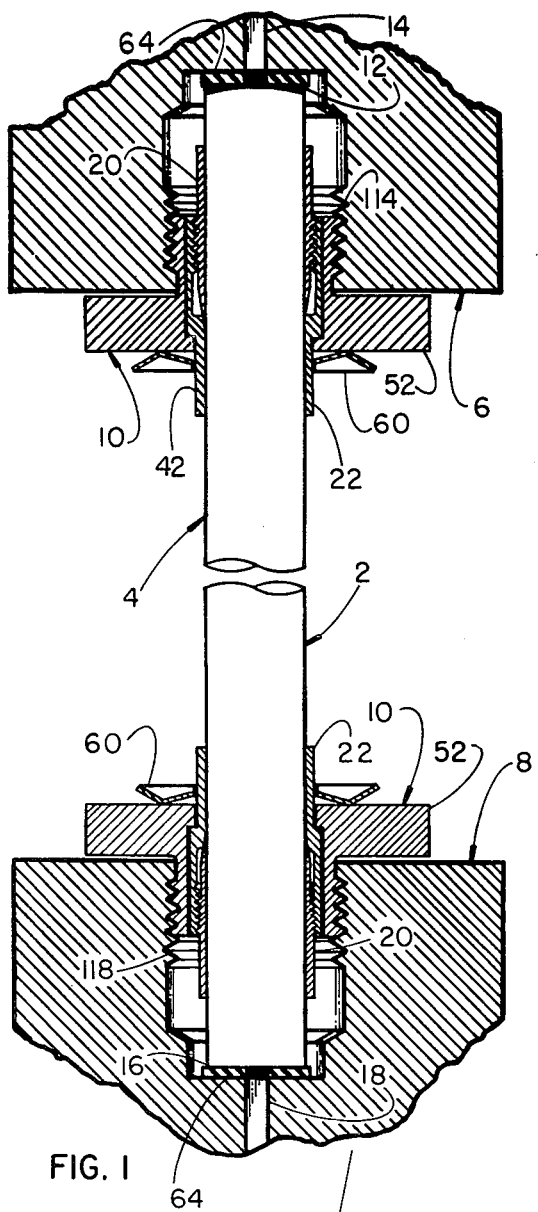
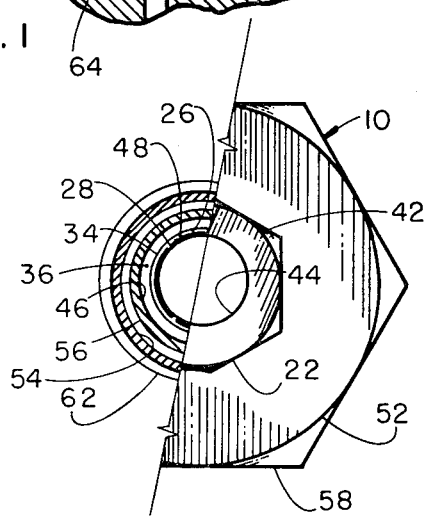
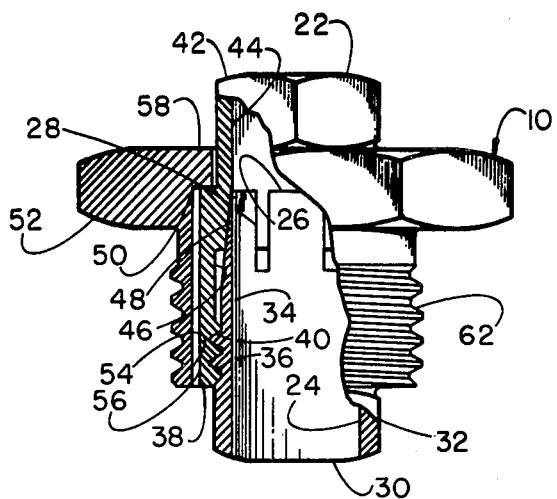
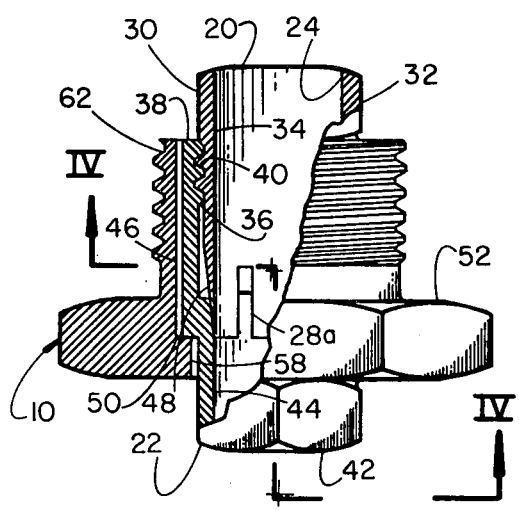
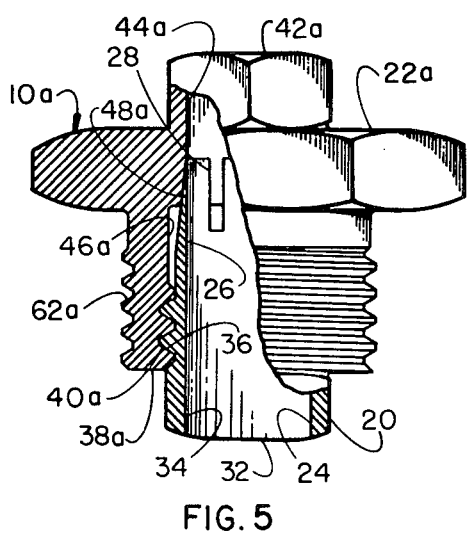
FIG. 1
FIG. 2
FIG. 3
FIG. 4
FIG. 5

COLUMN RETAINER

BACKGROUND OF THE INVENTION

1. Field of the Invention

This invention relates broadly to liquid chromatography apparatus (LCA). More particularly, it concerns retainer devices to permit the liquid chromatographic column (LCC) in LCA to be firmly held, without being deformed, marred or otherwise damaged, to permit the LCC to be connected to some other fluid flow member in the LCA, e.g., an injection value at the inlet end of the column and/or a detector at the outlet end of the column.

2. Description of the Prior Art

Liquid chromatographic columns are typically operated under relatively high pressures. In use these columns must be connected to other elements of the LCA so that high pressure liquids may flow from the other elements into the column, e.g., an injector valve, or flow from the column into other elements, e.g., a detector unit.

A number of different type connector devices and arrangements have been used in the past to make fluid-tight connections between the column and the other elements. Compression fittings well known for use as connectors for malleable tubing have been used to effect such connections. However, use of such fittings produces a permanent deformation of the column, e.g., where the compression ferrule is crimped in place. Also, the fitting is not removeable from the column without cutting it above the ferrule. Further, the deformation of the column can be great enough to damage a glass lined column.

Another approach to the column connection problem is to form male threads on the column to function with threaded female connectors (see U.S. Pat. No. 3,440,864). Such connection arrangements are relatively expensive because of the need to form the threads on the LCC and are not satisfactory with very small diameter tubing such as is used in micro liquid chromatography apparatus.

OBJECTS

A principal object of the present invention is the provision of new forms of liquid chromatography apparatus.

Further objects include the provision of:

1. Improved devices for connecting liquid chromatographic column ends to other fluid flow members in LCA.

2. Such improved connector devices that produce no permanent deformation of the liquid chromatographic column.

3. Such new devices that produce no modification of the liquid chromatographic column as occurs when the ferrule of a compression fitting is crimped to the column.

4. Such new devices that will not damage glass lined columns when used therewith.

5. Such new devices that do not mar the surface of the liquid chromatographic column.

6. Such new devices that are reuseable on the same or other columns.

Other objects and further scope of applicability of the present invention will become apparent from the detailed description given hereinafter; it should be understood, however, that the detailed description, while indicating preferred embodiments of the invention, is given by way of illustration only, since various changes and modifications within the spirit and scope of the invention will become apparent to those skilled in the art from this detailed description.

SUMMARY OF THE INVENTION

The foregoing objects are accomplished according to the present invention by the provision of liquid chromatography apparatus comprising a liquid chromatographic column having an inlet end and an outlet end, an external fluid flow member for connection to one of the ends of the column, a gasket between the fluid flow member and the one end of the column, and a column retainer assembly holding the column in pressure sealed engagement with the gasket and the gasket in turn with the fluid flow member.

The retainer assembly comprises an elongated collet and a collet nut. The collet has a lumen of substantially constant diameter throughout its length approximately equal to the O.D. of the column, a tapered proximal end with a plurality of longitudinal slits therein, an extended distal end, a central body portion integral with the distal end and the proximal end, and external threads on the central body portion.

The collet nut has a distal end internally threaded to mate with the external threads of the collet, an extended proximal end with a first lumen of diameter approximately equal to the O.D. of the column, a second lumen distal of the proximal end of diameter larger than the first lumen, and a internal tapered portion joining the first lumen to the second lumen. The column extends through the lumens of the collet and the collet nut and the collet nut is threaded into the collet to force the collet tapered proximal end into the collet nut internal tapered portion thereby forcing the collet proximal end into contact with the outside of the column.

In preferred embodiments of the invention, the external fluid flow member is a chromatography detector unit connected to the outlet end of the column and/or is an injection valve connected to the inlet end of the column.

Also in preferred embodiments of the invention, the collet nut proximal end comprises a shoulder, the fluid flow member has an internally threaded opening for making the connection to the column, there is a retainer nut with external threads that are threaded into a threaded opening in the fluid flow member and the retainer nut bears on the collet nut shoulder to thrust the retainer assembly toward the fluid flow member.

BRIEF DESCRIPTION OF THE DRAWINGS

A more complete understanding of the invention may be had by reference to the accompanying drawings wherein like elements are designated by the same numeral and in which:

FIG. 1 is a fragmentary side elevation of liquid chromatography apparatus constructed according to the invention.

FIG. 2 is an enlarged, fragmentary lateral sectional view of one embodiment of a column retainer of the invention.

FIG. 3 is an enlarged, fragmentary lateral sectional view of another embodiment of column retainer of the invention.

FIG. 4 is a sectional view taken on the line IV—IV of FIG. 3.

FIG. 5 is a fragmentary, lateral view sectional view of another embodiment of a column retainer of the invention.

DESCRIPTION OF PREFERRED EMBODIMENTS

Referring in detail to the drawings, the liquid chromatography apparatus 2 comprises a liquid chromatographic column 4, an injector valve 6, a detector unit 8 and a column retainer assembly 10.

The liquid chromatographic column 4 has an inlet end 12 connected to the injector valve 6 at its outlet 14 and a outlet end 16 connected to the detector unit 8 at its inlet 18.

The column retainer assembly 10 comprises an elongated collet 20 and a collet nut 22. The collet 20 has a lumen 24 of substantially constant diameter throughout its length approximately equal to the O.D. of the column 4, a tapered proximal end 26 with a plurality of longitudinal slits 28 therein, an extended distal end 30 bearing wrench flats 32, a central body portion 34 integral with the proximal end 26 and the distal end 30, and external threads 36 on the central body portion 34.

The collet nut 22 has a distal end 38 having internal threads 40 to mate with the external threads 36 of the collet 20, a proximal end 42 with a first lumen 44 of diameter approximately equal to the O.D. of the column 4, a second lumen 46 distal of the proximal end 42 of diameter larger than the first lumen 44, and a internal tapered portion 48 joining the first lumen 44 to the second lumen 46.

The column 4 extends through the lumens of the collet 20 and the collet nut 22 and the collet 20 is threaded into the collet nut 22 forcing the collet tapered proximal end 26 into the collet nut internal tapered portion 48 thereby clamping the collet proximal end 26 onto the outside of the column 4.

The collet nut proximal end 42 comprises a shoulder 50. The retainer nut 52 has a lumen 54 that permits it to slip over the outside 56 of the collet nut 22 until the radial, end lug 58 engages the shoulder 50 of the collet nut 22. A retaining ring 60 is used to hold the retaining nut 52 in this position on the collet nut 22.

At the inlet end 12 of the column 4, external threads 62 on the outside of the retainer nut 52 thread into the internal thread 114 of outlet 14 of the injector valve 6 and the retainer nut lug 58 bears on the shoulder 50 of the collet nut 22 to thrust the column inlet end 12 into the the outlet 14 against the gasket 64 to make a fluid tight connection between the column 4 and the injector valve 6.

At the outlet end 16 of the column 4, external threads 62 on the outside of the retainer nut 52 thread into the internal thread 118 of inlet 18 of the detector 8 and the retainer nut lug 58 bears on the shoulder 50 of the collet nut 22 to thrust the column outlet end 16 into the the inlet 18 against the gasket 64 to make a fluid tight connection between the column 4 and the detector 8.

The assembly 10 of FIG. 3 corresponds to the assembly 10 connected to the injector valve 6 of FIG. 1 and the assembly 10 of FIG. 2 corresponds to the assembly 10 connected to the detector unit 8. The embodiment of FIG. 2 can differ, for example, from that of FIG. 3 by having the slots 28 of FIG. 2 narrower and longer than the related slots 28a of FIG. 3.

The column retainer assembly 10a shown in FIG. 5 differs from the assembly 10 of FIG. 2 by not including a retainer nut 52. Instead, the collet nut 22a is provided with both internal threads 40a and external threads 62a. The internal threads 40a serve like the threads 40 of collet nut 22 to clamp the proximal end 26a of collet 20 onto the column 4. The external threads 62a serve like the threads 62 of retainer nut 52 to connect the retainer assembly 10a to an injector valve 6, detector unit 8 or other external fluid flow element.

In the initial assembly of collets 20 and collet nuts 22 upon the column 4, the extended ends 30 of the collets 20 and extended ends 42 of collet nuts 22 serve as means for holding the collets 20 and nuts 22 while tightening them on the column 4 since they comprise flats to accomodate a wrench or like tightening tool.

The embodiments of the invention in which an exclusive property or privilege is claimed are defined as follows:

1. Liquid chromatography apparatus comprising:
   a liquid chromatographic column having an inlet end and an outlet end,
   an external fluid flow member for connection to one of said ends of said column,
   a gasket between said fluid flow member and said one end of said column, and
   a column retainer assembly holding said column in pressure sealed engagement with said gasket and said gasket in turn with said fluid flow member,
   said retainer assembly comprising an elongated collet and a collet nut,
   said collet having:
     a lumen of substantially constant diameter throughout its length approximately equal to the O.D. of said column,
     a tapered proximal end with a plurality of longitudinal slots therein,
     an extended distal end,
     a central body portion integral with said distal end and said proximal end, and
     external threads on said central body portion, said collet nut having:
     a distal end internally threaded to mate with said external threads of said collet,
     a proximal end with a first lumen of diameter approximately equal to the O.D. of said column,
     a second lumen distal of said first lumen of diameter larger than said first lumen, and
     a internal tapered portion joining said first lumen to said second lumen,
   said column extending through said lumens of said collet and said collet nut and said collet nut is threaded into said collet to force said collet tapered proximal end into said collet nut internal tapered portion clamping said collet proximal end onto the outside of said column.

2. The apparatus of claim 1 wherein said external fluid flow member is a chromatography detector unit connected to said outlet end of said column.

3. The apparatus of claim 1 wherein said external fluid flow member is an injection valve connected to said inlet end of said column.

4. The apparatus of claim 1 wherein said collet nut proximal end comprises a shoulder, said fluid flow member has an internally threaded opening for making said connection to said column, there is a retainer nut with external threads that are threaded into said threaded opening in said fluid flow member and said retainer nut bears on said shoulder to thrust said retainer assembly toward said fluid flow member.

* * * * *